United States Patent [19]

Lawrie et al.

[11] Patent Number: 4,907,455
[45] Date of Patent: Mar. 13, 1990

[54] CERAMIC DELAY LINES FOR HOT ULTRASONIC EXAMINATION

[75] Inventors: William E. Lawrie, Concord, Va.; Daniel R. Petrak, Midland, Mich.

[73] Assignee: The Babcock & Wilcox Company, New Orleans, La.

[21] Appl. No.: 198,409

[22] Filed: May 25, 1988

[51] Int. Cl.$^4$ ............................................. G01N 29/04
[52] U.S. Cl. ..................................................... 73/644
[58] Field of Search .......................... 73/644; 310/336

[56] References Cited

U.S. PATENT DOCUMENTS

| 2,467,301 | 4/1949 | Firestone . | |
|---|---|---|---|
| 2,697,936 | 12/1954 | Farrow . | |
| 3,550,435 | 12/1970 | Kaule . | |
| 3,747,398 | 7/1973 | Rathburn et al. . | |
| 4,182,155 | 1/1980 | Fowler . | |
| 4,437,332 | 3/1984 | Pittaro . | |
| 4,559,827 | 12/1985 | Kupperman et al. | 73/644 |
| 4,783,997 | 11/1988 | Lynnworth | 73/644 |

FOREIGN PATENT DOCUMENTS 53-37488  4/1978  Japan ...................................... 73/644

OTHER PUBLICATIONS

MACOR TM, Corning Glass Works, Corning, N.Y. 14830, Apr. 1978.

Primary Examiner—John Chapman
Attorney, Agent, or Firm—Vytas R. Matas; Robert J. Edwards; Daniel S. Kalka

[57] ABSTRACT

An ultrasonic transducer arrangement for inspecting a work piece at an elevated temperature through the use of ceramic delay lines is disclosed. The ceramic material utilized for the delay lines is comprised of a composition of silicon nitride and boron nitride which is hot pressed so that the boron nitride platelets are aligned substantially parallel to the propagation direction of the ultrasonic pulses thus minimizing pulse attenuation. The ceramic material is heat and wear resistant and can be machined so as to conform to the surface of the work piece being inspected.

3 Claims, 2 Drawing Sheets

CERAMIC DELAY LINES FOR HOT ULTRASONIC EXAMINATION

TECHNICAL FIELD

The present invention generally relates to ultrasonic testing apparatus, and more particularly to ceramic delay lines for use with an ultrasonic transducer arrangement when inspecting a work piece at an elevated temperature.

BACKGROUND ART

During the welding of pressure vessels, the weldment must be maintained at preheat temperatures until the welding process has been completed and the vessel has been stressed relieved. Minimum preheat temperature is approximately 300° F. but typically temperatures between 400° F. to 450° F. exist. In thick section welding, it is advantageous to inspect the weld during the welding process to detect defects before they are covered by more weld material. In addition, in making difficult welds where defects are quite possible, hot ultrasonic inspection allows repairs to be made without using stress relief time.

Ultrasonic testing of welds at preheat temperatures requires that delay lines be used to protect the transmit transducer and the receive transducer from the high temperatures. The material utilized for the delay lines should have low ultrasonic attenuation and should be readily machineable so as to be conformable to the surface being inspected. Plastics are typically used for delay lines, but at preheat temperatures, plastics exhibit excessive attenuation.

In view of the foregoing, it has become desirable to develop a delay line material which can withstand high temperatures, is machineable, exhibits low ultrasonic attenuation, and is wear resistant.

SUMMARY OF THE INVENTION

The present invention solves the problems associated with the prior art and other problems by utilizing a ceramic material for the delay line. The ceramic material is comprised of a composition of silicon nitride and boron nitride. The resulting composition is hot pressed so that the boron nitride platelets are aligned substantially parallel to the propagation direction of the ultrasonic pulses. With such an orientation, attenuation of the ultrasonic pulses is minimized. The resulting material is readily machineable so as to be conformable to the surface of the work piece being inspected. In addition, since the material is a ceramic, the resulting delay line is extremely wear resistant and can be used at elevated temperatures without any harmful effects.

DESCRIPTION OF THE PREFERRED EMBODIMENT

Figure 1:
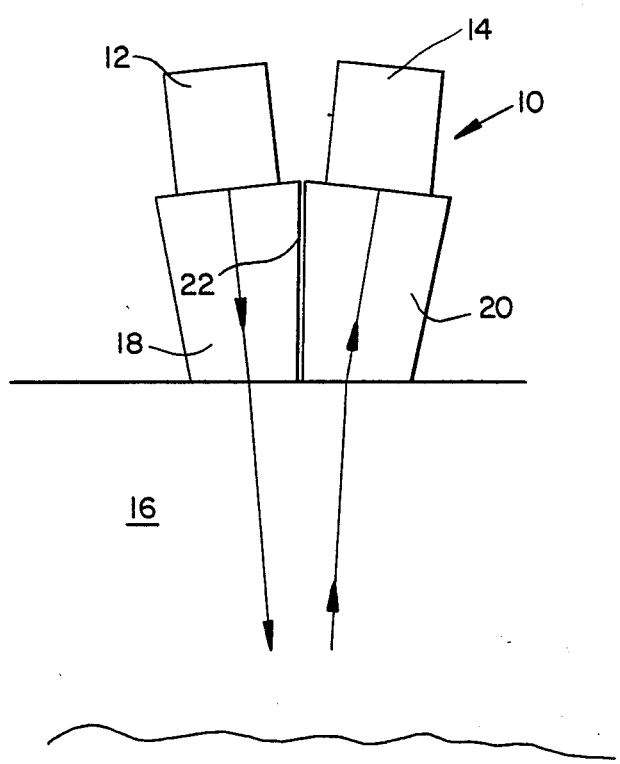
FIG. 1 is a front elevation view of the present invention illustrating a dual-element transducer arrangement in conjunction with ceramic delay lines.

Referring now to the drawings where the illustrations are for the purpose of describing the preferred embodiment of the present invention and are not intended to limit the invention hereto, FIG. 1 is a front elevation view of the present invention using a dual-element transducer arrangement 10. This transducer arrangement 10 includes a transmit transducer 12 and a receive transducer 14 which are coupled to the entrance surface of a work piece 16 for transmitting an ultrasonic signal into the work piece 16 and for receiving "echo" return signals therefrom. Ceramic delay lines (standoffs) 18 and 20 are provided to couple the transmit transducer 12 and the receive transducer 14, respectively to the work piece 16. The ceramic delay lines 18 and 20 are acoustically isolated from each other by a sound absorbing barrier 22, such as cork to prevent the ultrasonic signals from passing directly from one delay line to the other delay line. An alternative method is to separate the delay lines using narrow spacers at each side. The resultant air gap between the delay lines provides the desired isolation. The delay lines 18 and 20 are wedge shaped in order to permit the receive transducer 14 to intercept any ultrasonic pulses reflected by the work piece 16.

The transmit transducer 12 and the receive transducer 14 each include a piezoelectric element. Application of a voltage pulse to the transmit transducer 12 causes its piezoelectric element to transmit a pressure pulse through the ceramic delay line 18 into the surface of the work piece 16 to be examined. The existence of a defect or other acoustic discontinuity in the work piece 16 causes the pressure pulse to be reflected toward the receive transducer 14 where it is intercepted by the piezoelectric element therein. Interception of the reflected pressure pulse by the piezoelectric element in the receive transducer 14 causes the element to convert the pressure pulse into a voltage pulse. By measuring the total elapsed time of travel between the initial pressure pulse and the reflected pressure pulse, and by considering the acoustic velocity of the work piece and the ceramic delay lines 18 and 20, the location of the defect or discontinuity within the work piece 16 can be determined. Conversely, if the location of the defect or discontinuity is known or if the thickness of the work piece 16 is known, the acoustic velocity of the work piece 16 can be determined.

Figure 2:
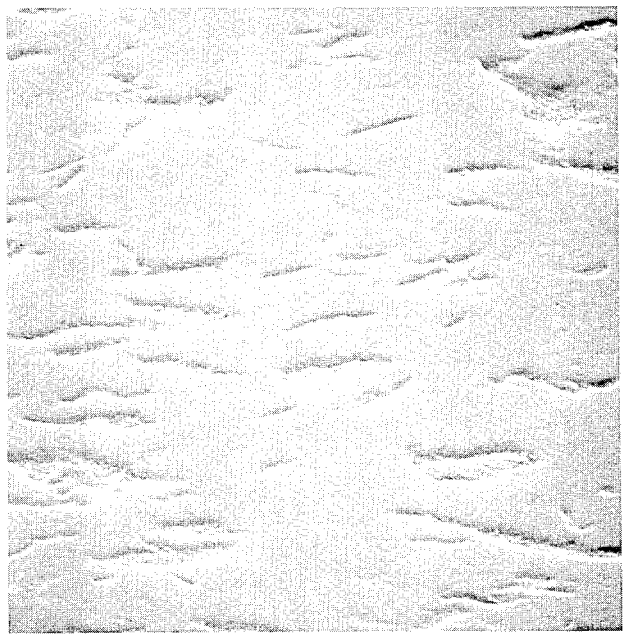
FIG. 2 is an optical photomicrograph of a cross section of a composition of hot pressed silicon nitride and boron nitride, and illustrating the boron nitride platelets therein.

The ceramic delay lines 18 and 20 are produced from a high quality machineable ceramic material composed of silicon nitride with 30% boron nitride. This material is machineable, has good ultrasonic properties, and retains its elastic properties at high temperature. The material is formed by hot pressing the foregoing composition into flat billets in such a manner that the boron nitride platelets are aligned in the material, as shown in FIG. 2. The design of the delay lines 18 and 20 incorporates the platelet orientation in that the pressure pulses from the transmitting piezoelectric element and to the receiving piezoelectric element should be propagated substantially parallel to the orientation of the platelets, thus reducing ultrasonic pulse attenuation due to scattering. Ultrasonic transmission in a direction that is at a right angle to the orientation of the platelets, i.e., in the direction of hot pressing, would be highly attenuated. Thus, the orientation of the platelets should be substantially parallel to the direction of propagation through the delay lines 18 and 20 in order to minimize ultrasonic pulse attenuation.

One of the major advantages of the present invention is that the elastic properties of the ceramic delay lines 18 and 20 are not degraded at preheat temperatures (300°–450° F.). Thus, usable ultrasonic data can be obtained as long as the delay lines 18 and 20 are coupled to the surface of the work piece 16. In contrast, such ultrasonic pulses typically disappear after ten seconds using other available delay lines. In addition, inasmuch as the ceramic material utilized for the delay lines 18 and 20 is readily machineable, the end of the delay lines can be machined so as to conform to a specific surface contour, i.e., the ends can be machined to fit curved surfaces. In addition, holes can be tapped in the material so that the delay lines can be attached, if necessary, to other devices and/or fixtures.

Another important advantage of the present invention is that the acoustic impedance of the ceramic material utilized for the delay lines 18 and 20 provides a good impedance match to both the piezoelectric elements used within the transmit transducer 12 and the receive transducer 14 and the material comprising the work piece 16 being inspected. Such a good impedance match results in a high signal-to-noise ratio, minimal attenuation of the ultrasonic pulses, and accurate measurements of the location of defects and/or discontinuities in the material being inspected.

Certain modifications and improvements will occur to those skilled in the art upon reading the foregoing. It should be noted that all such modifications and improvements have been deleted herein for the sake of conciseness and readability, but are properly within the scope of the following claims.

We claim:

1. An apparatus for the ultrasonic inspection of a workpiece at a high temperature, comprising:
   a first transducer including an ultrasonic pulse generating source;
   a second transducer for receiving ultrasonic pulses reflected from the workpiece being inspected;
   a first coupling means interposed between said first transducer and the workpiece being inspected; and
   a second coupling means interposed between the workpiece being inspected and said second transducer, said first and second coupling means being formed by hot pressing a composition of silicon nitride and boron nitride, the composition having boron nitride platelets oriented substantially perpendicularly to the direction of the hot pressing, said first and second coupling means being oriented so that the boron nitride platelets in the composition are substantially parallel to the direction of propagation of the ultrasonic pulses produced by said pulse generating source and to the direction of propagation of said ultrasonic pulses reflected from the workpiece being inspected.

2. A ceramic delay line for an ultrasonic transducer arrangement for ultrasonically examining a workpiece with the ceramic delay line being interposed between the transducer arrangement and the workpiece being inspected, the ceramic delay line comprising a composition of silicon nitride and boron nitride with the composition of the ceramic delay line having platelets substantially aligned therein, the ceramic delay line being situated so that the platelets in the composition are substantially parallel to the direction of propagation of ultrasonic pulses produced by the ultrasonic transducer arrangement and to the direction of propagation of ultrasonic pulses reflected from the workpiece being inspected.

3. A ceramic delay line, as recited in claim 2, wherein the composition consists essentially of approximately 70% silicon nitride and approximately 30% boron nitride.

* * * * *